(12) United States Patent
Choi et al.

(10) Patent No.: US 8,318,455 B2
(45) Date of Patent: Nov. 27, 2012

(54) INDUCIBLE/REGULATED GENE EXPRESSION SYSTEM IN E COLI

(76) Inventors: Young Jun Choi, Ile Bizard (CA); Bernard Massie, Laval (CA); Carlos B. Miguez, Beaconsfield (CA)

(*) Notice: Subject to any disclaimer, the term of this patent is extended or adjusted under 35 U.S.C. 154(b) by 549 days.

(21) Appl. No.: 12/452,232

(22) PCT Filed: May 14, 2008

(86) PCT No.: PCT/CA2008/000900
§ 371 (c)(1), (2), (4) Date: Dec. 22, 2009

(87) PCT Pub. No.: WO2009/000063
PCT Pub. Date: Dec. 31, 2008

(65) Prior Publication Data
US 2010/0112636 A1    May 6, 2010

Related U.S. Application Data

(60) Provisional application No. 60/929,389, filed on Jun. 25, 2007.

(51) Int. Cl.
*C12P 21/02* (2006.01)
(52) U.S. Cl. ............... 435/69.1; 435/320.1; 435/252.33; 536/24.1

(58) Field of Classification Search .................. None
See application file for complete search history.

(56) References Cited

U.S. PATENT DOCUMENTS 5,356,796 A * 10/1994 Keller ................. 435/69.1
6,939,959 B2 * 9/2005 Hu ..................... 536/24.1

OTHER PUBLICATIONS

Eaton, J. Bacteriol. (1997) vol. 179, pp. 3171-3180.*

* cited by examiner

*Primary Examiner* — Jim Ketter
(74) *Attorney, Agent, or Firm* — Hans Koenig

(57) ABSTRACT

An expression system for transforming E coll with a nucleic acid molecule of interest has an operator sequence of a cmt operon operatively linked to a promoter for the operator, and, a repressor sequence from a cym operon operatively linked to a promoter for the repressor. The expression system may have a nucleic acid molecule of interest, for example, a nucleic acid molecule that encodes a protein. Any type of E coll host cells may be transformed with the expression system. A method of producing a protein involves transforming an E coll host cell with the expression system having a nucleic acid molecule that codes for a protein, and, culturing the host cell in a culture medium under conditions in which the nucleic acid molecule will express the protein.

12 Claims, 9 Drawing Sheets

SEQUENCE LISTING

<160> NUMBER OF SEQ ID NOS: 14

<210> SEQ ID NO 1
<211> LENGTH: 92
<212> TYPE: DNA
<213> ORGANISM: Artificial
<220> FEATURE:
<223> OTHER INFORMATION: Primer

<400> SEQUENCE: 1
cgagctcaaa tcataaaaaa tttatttgct ttgtgagcgg ataacaatta taatagattc    60
aacaaacaga caatctggtc tgtttgtatt at    92

<210> SEQ ID NO 2
<211> LENGTH: 31
<212> TYPE: DNA
<213> ORGANISM: Artificial
<220> FEATURE:
<223> OTHER INFORMATION: Primer

<400> SEQUENCE: 2
cgcatgctca gttgtacagt tcatccatgc c    31

<210> SEQ ID NO 3
<211> LENGTH: 181
<212> TYPE: DNA
<213> ORGANISM: Artificial
<220> FEATURE:
<223> OTHER INFORMATION: Primer

<400> SEQUENCE: 3
cacgcgtccg gaattgccag ctggggcgcc ctctggtaag gttgggaagc cctgcaaagt    60
aaactggatg gctttcttgc cgccaaggat ctgatggcgc aggggatcaa gatctgatca   120
agagacagga tgaggatcgt ttcgcaagat ggtgatcatg agtccaaaga gaagaacaca   180
g    181

<210> SEQ ID NO 4
<211> LENGTH: 36
<212> TYPE: DNA
<213> ORGANISM: Artificial
<220> FEATURE:
<223> OTHER INFORMATION: Primer

<400> SEQUENCE: 4
cacatgtcta gcgcttgaat ttcgcgtacc gctctc    36

<210> SEQ ID NO 5
<211> LENGTH: 40
<212> TYPE: DNA
<213> ORGANISM: Artificial

```
<220> FEATURE:
<223> OTHER INFORMATION: Primer

<400> SEQUENCE: 5
cgctagcatg agcaacaaga acaatgaaga cctgcagcgc                                40

<210> SEQ ID NO 6
<211> LENGTH: 34
<212> TYPE: DNA
<213> ORGANISM: Artificial
<220> FEATURE:
<223> OTHER INFORMATION: Primer

<400> SEQUENCE: 6
gcaattgtca acgttcgtgg acataggtcc ctgg                                      34

<210> SEQ ID NO 7
<211> LENGTH: 37
<212> TYPE: DNA
<213> ORGANISM: Artificial
<220> FEATURE:
<223> OTHER INFORMATION: Primer

<400> SEQUENCE: 7
cgctagcatg cgagagaaac aggtgtcggg agccttg                                   37

<210> SEQ ID NO 8
<211> LENGTH: 34
<212> TYPE: DNA
<213> ORGANISM: Artificial
<220> FEATURE:
<223> OTHER INFORMATION: Primer'

<400> SEQUENCE: 8
gcaattgtca gcgcacgtgc acgtaggtgc cggg                                      34

<210> SEQ ID NO 9
<211> LENGTH: 31
<212> TYPE: DNA
<213> ORGANISM: Artificial
<220> FEATURE:
<223> OTHER INFORMATION: Primer

<400> SEQUENCE: 9
cgctagcatg gaacatagag cgttcaagtg g                                         31

<210> SEQ ID NO 10
<211> LENGTH: 32
<212> TYPE: DNA
<213> ORGANISM: Artificial
<220> FEATURE:
<223> OTHER INFORMATION: Primer

<400> SEQUENCE: 10
cgagctctta cagcttgacg acgagtacgc cg                                        32

<210> SEQ ID NO 11
<211> LENGTH: 34
<212> TYPE: DNA
<213> ORGANISM: Artificial
<220> FEATURE:
<223> OTHER INFORMATION: Primer

<400> SEQUENCE: 11
cgctagcatg gatcaatcta aaacaaatca aaac                                      34
```

```
<210> SEQ ID NO 12
<211> LENGTH: 31
<212> TYPE: DNA
<213> ORGANISM: Artificial
<220> FEATURE:
<223> OTHER INFORMATION: Primer

<400> SEQUENCE: 12
cgagctctta tttatttgta ataccgtctg c                              31

<210> SEQ ID NO 13
<211> LENGTH: 32
<212> TYPE: DNA
<213> ORGANISM: Artificial
<220> FEATURE:
<223> OTHER INFORMATION: Primer

<400> SEQUENCE: 13
cgctagcatg gcaacttcaa ctaaaaaatt ac                             32

<210> SEQ ID NO 14
<211> LENGTH: 34
<212> TYPE: DNA
<213> ORGANISM: Artificial
<220> FEATURE:
<223> OTHER INFORMATION: Primer

<400> SEQUENCE: 14
gcaattgtta ttgtaaatac tcttctggaa tcgg                           34
```

INDUCIBLE/REGULATED GENE EXPRESSION SYSTEM IN E COLI

CROSS-REFERENCE TO RELATED APPLICATIONS

This application is a national entry of PCT/CA2008/000900 filed May 14, 2008, which claims the benefit of U.S. Provisional Patent Application Ser. No. 60/929,389 filed Jun. 25, 2007, which is herein incorporated by reference in its entirety.

FIELD OF THE INVENTION

The present invention relates to biotechnology, in particular to gene expression systems in Escherichia coli.

BACKGROUND OF THE INVENTION

New hosts and expression vectors for the production of industrially important recombinant protein are continuously being developed for the purpose of increasing production yields and simplifying down stream processes such as single-step purification using affinity tag systems. Though many expression hosts are available, Escherichia coli continues to remain one of the most frequently employed host for the mass production of various useful recombinant proteins or peptides, and many promoters such as $P_{lac}$, $P_{trp}$, $P_{tac}$, $\lambda P_L$, $P_{T7}$ and $P_{BAD}$ are commonly utilized for the construction of expression vectors (Baneyx, 1999). Among these, lacUV5, tac and combined system of $P_{T7}$ with lacUV5 are widely used, because the expression can easily be regulated by varying the concentration of the inducer isopropyl-beta-D-thiogalactopyranoside (IPTG, Schein and Noteborn, 1988). However, the use of IPTG precludes the use of these expression systems in pilot scale production of recombinant proteins, mainly due to the high cost and potential toxicity of IPTG (Figge et al., 1988, Kosinski et al., 1992, Bhandari and Gowrishankar, 1997, Leigh et al., 1998, Yogender et al., 2001, Wang et al., 2004). Other promoters called λPL and λPR are generally induced by a temperature shift, which can have an adverse effect on the protein folding and reduce the final yield of the product (Remaut et al., 1981).

It is known that the expression of a homologous or heterologous gene may be enhanced by replacing a promoter sequence naturally associated with that gene with a strong promoter sequence, which results in an enhanced expression of the gene at the transcriptional level (Studier and Moffatt, 1986, Gupta et al., 1999). However, ideal expression system should provide high-level expression under induced conditions and no basal expression under repressed conditions, yet should show adjustability to intermediate levels over a wide range of inducer concentrations (Rossi and Blau, 1998, Keyes and Mills, 2003). To date, only a limited number of expression system have been explored for the industrial recombinant protein production. The field of modern biotechnology is competitive and is attracting considerable interest from industrial partners outside the traditional fermentation industry, interested in the industrial applications of enzymes and other proteins. Therefore, it is not surprising that several of these partners have started to explore the possibility of using new expression systems as alternatives to those covered by patents and patent application (Staub, et al., 2002). It is in the interest of the biotechnological industry to seek new expression systems, which are easily accessible, cheap and simple to regulate. Especially, systems that are independent of the host strain, medium, and growth rate are needed. Therefore, the aim of our work was to develop a next generation of a novel expression system which fulfills most of factors to be an ideal expression system of E. coli.

The ability to produce high biomass densities of E. coli in fermentors (Lee, 1996, Thiry and Cingolani, 2002), combined with the newly adopted regulatory genetic elements obtained from Pseudomonas putida F1 (Choi et al., 2006), renders this novel expression system extremely interesting as a potential tool for the production of recombinant proteins and of industrially important bulk chemicals. The applications of such an expression system is equally comprehensive encompassing the: (1) production of research reagents to support R&D in biotechnology and in various biological fields including proteomics; (2) production of commercial recombinant proteins (enzymes and bio-active peptides); (3) production of various biomaterials including proteinaceous and non-proteinaceous bio intermediates; (4) as a tool for metabolic engineering work.

International Patent Publication WO 2007/022623 published Mar. 1, 2007 discloses the use of regulating elements from Pseudomonas putida to enable inducible regulation of gene expression in Methylobacterium extorquens. International Patent Publication WO 2006/037215 published Apr. 13, 2006 discloses the use of cumate inducible regulating elements to enable inducible regulation of gene expression in Chinese Hamster Ovary (CHO) cells. In both of these cases, the repressor and its weak promoter are incorporated into the genome of the host cell separately from the plasmid containing the gene of interest, operator and promoter for the operator.

There is a need for a tightly regulated, inducible gene expression system in Escherichia coli.

SUMMARY OF THE INVENTION

A novel inducible expression system, designated pNEW, is disclosed carrying a synthetic operator of Pseudomonas putida and expression profiles of nucleic acid molecules of interest. The expression system comprises an operator and repressor complex that is activated by cumate and like inducers, leading to regulated gene expression over several orders of magnitude.

Thus, there is provided an expression system for transforming E. coli with a nucleic acid molecule of interest, the vector comprising: an operator sequence of a cmt operon operatively linked to a promoter for the operator; and, a repressor sequence from a cym operon operatively linked to a promoter for the repressor.

The expression system may further comprise the nucleic acid molecule of interest, which may be, for example, an antisense inhibitor of gene expression, a nucleic acid coding for a protein, or any other nucleic acid molecule for which expression is desired in E. coli. Preferably, the nucleic acid molecule encodes a protein.

There is further provided an E. coli host cell transformed with an expression system of the present invention.

There is further provided a method of producing a protein comprising transforming an E. coli host cell with an expression system of the present, the nucleic acid molecule of the expression system coding for a protein; and, culturing the host cell in a culture medium under conditions in which the nucleic acid molecule will express the protein.

Expression of the nucleic acid molecule of interest in E. coli is activated by addition of an inducer. The inducer may comprise, for example, p-cumate, butyrate, dimethyl-p-aminobenzoic acid (DM PABA), trimethyl cumate, ethylbenzoate, a salt thereof or a combination thereof. p-Cumate is preferred.

A tightly regulated gene expression system in *Escherichia coli* of the present invention may include regulatory elements of the *Pseudomonas putida* F1 cym and cmt operons to control target gene expression at the transcriptional level by using p-cumate as an inducer in any type of *E. coli* strains. This expression system includes a specific expression vector, pNEW, that may contain a partial T5 phage promoter combined with the P1 synthetic operator and the cymR repressor protein encoding gene designed to express constitutively in the host strain. The induction of transcription relies on the addition of the exogenous inducer, e.g. p-cumate, which is non-toxic, inexpensive and easy to use. High concentrations of recombinant protein accumulation are observed (generally, 40-85% of total cellular protein), which is a more than 10,000-fold induction in stably transformed cells on average. Both high induction of transcription and extremely low basal expression allowed extremely high induction levels, with a degree of control that is far superior to other currently available *E. coli* expression systems, for example the T7 system with IPTG inducer. The results indicated that the present pNEW expression system is a highly efficient system for the potential production of recombinant proteins in any type of *E. coli* strains, especially when cloned proteins have growth inhibitory or toxic effects to host cell metabolism.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Materials and Methods

Figure 1:
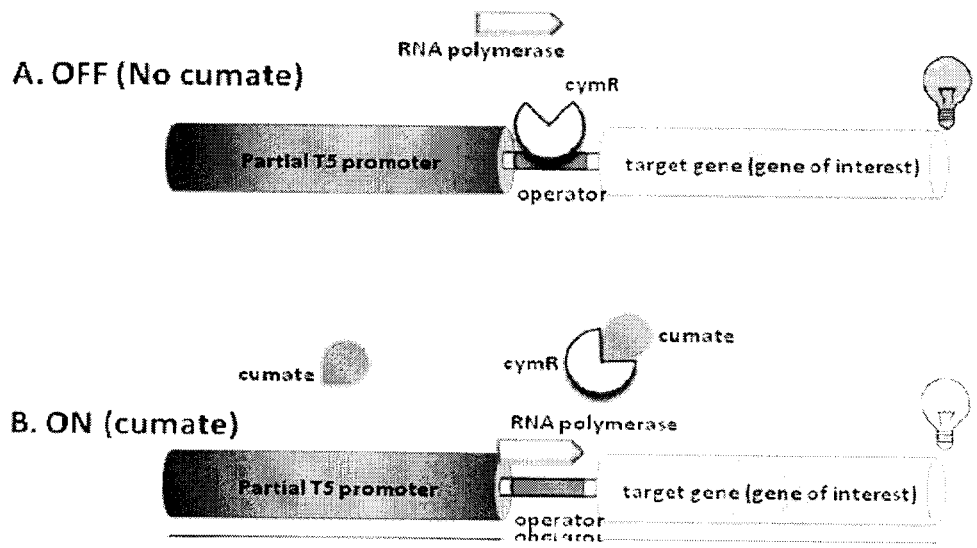
FIG. 1 is a schematic diagram of the mechanism of action of the cumate-switchable expression system.

Bacterial strains and growth conditions. The bacterial strains and plasmids used in this study are listed in Table 1. *E. coli* strains DH5α, S17-1 λ/pir, K12, Top10, and BL21(DE3), were used for the heterologous gene expression host. Especially, *E. coli* strain Top10 was used for cloning and propagation of recombinant DNA and some target protein expression host. *E. coli* was cultured in Luria Bertani broth (LB) at 37° C. and media were solidified by 1.8% agar (Difco) when appropriate. Antibiotics were used at the following concentrations (in μg/ml): ampicillin, 100; kanamycin (Km), 50; tetracyclin (Tc), 35.

Benchtop Fermentations. Batch fermentation experiments were carried out in a 14-l bioreactor (BioFlo 110, New Brunswick Scientific, Edison, N.J. USA) to compare GFP production yield between T7 expression system and cumate system. For the batch culture, pre-cultures were used to inoculate the bioreactor filled with 5 l of medium A (Yoon et al, 2003) and initial O.D. was adjusted to 0.1 for both expression systems. The cultures induced with IPTG for T7 system and cumate for cumate system when O.D. reached at 38 to 42. For cultures carried out in bioreactors, pH and dissolved oxygen were controlled at 7 and 25%, respectively.

Construction of expression vector. The operator sequence of cmt operon from *P. putida* F1 was introduced downstream of the phage T5 promoter (Bujard, et al. 1987) by polymerase chain reaction (PCR). The pNEW regulative expression vector was obtained in several steps: first, the $P_{T5}$ synthetic operator sequence (OP)-GFP was PCR-amplified from pCUM-gfp (Choi, et al. 2006) using primers T5-OP-F-SAC (5'-C GAGCTCAA ATC ATA AAA AAT TTA TTT GCT TTG TGA GCG GAT AAC AAT TAT AAT AGA TTC AAC AAA CAG ACA ATC TGG TCT GTT TGT ATT AT-3') (SEQ ID NO: 1) (the SacI site is underlined, partial T5 promoter is boxed and operator site is in bold) and GFP-SPH-R (5'-C GCATGCTC AGT TGT ACA GTT CAT CCA TGC C-3') (SEQ ID NO: 2) (the SphI site is underlined). The 954 bp PCR fragment containing $P_{T5}$-operator-gfp was cloned into pCR2.1 to create pCR-T5OP. Next, a 954 bp SacI-SphI fragment from pCR-T5OP was then ligated between the SacI-SphI sites of pET36 (Novagen) to form pNEW-pre.

Subsequently, the $P_{km}$-cymR was amplified by PCR from pBRI-cymR1 (Choi et al. 2006) using primers PKM-CYM-MLU-F (5'-CACGCGTCC GGA ATT GCC AGC TGG GGC GCC CTC TGG TAA GGT TGG GAA GCC CTG CAA AGT AAA CTG GAT GGC TTT CTT GCC GCC AAG GAT CTG ATG GCG CAG GGG ATC AAG ATC TGA TCA AGA GAC AGG ATG AGG ATC GTT TCG CAA GAT GGT GAT CAT GAG TCC AAA GAG AAG AAC ACA G-3') (SEQ ID NO: 3) (the MluI site is underlined) and CYM-PCI-R (5'-C ACATGTCT AGC GCT TGA ATT TCG CGT ACC GCT CTC-3') (SEQ ID NO: 4) (the PciI site is underlined). The PCR product containing $P_{km}$-cymR was then cloned into pCR2.1 to create pCR-Pkm-cymR, and MluI-PciI fragment from pCR-$P_{km}$-cymR was ligated to the pNEW-pre digested by the same enzymes to generate pNEW-gfp.

Other reporter gene cloning. In order to validate heterologous protein production using newly developed cumate switch system (pNEW system), we have tested GFP, polyhydroxyalkanoic acids synthetase (PhaC1 and PhaC2), lactase, esterase and synthetic thrombin inhibitory peptides. To clone PhaC1 and PhaC2 genes from *Pseudomonas fluorescens* GK13, the genomic DNA was isolated, and the chromosome was subjected to PCR using the primers PhaC1FNhe (5'-CGCTAGCAT GAG CAA CAA GAA CAA TGA AGA CCT GCA GCG C-3') (SEQ ID NO: 5) (the NheI site is underlined), PhaC1RMFE (5'-GCAATTGTC AAC GTT CGT GGA CAT AGG TCC CTG G-3') (SEQ ID NO: 6) (the MfeI site is underlined), for PhaC1 and PhaC2FNhe (5'-CGCTAGCAT GCG AGA GM ACA GGT GTC GGG AGC CTT G-3') (SEQ ID NO: 7) (the NheI site is underlined), PhaC2RCla (5'-GCAATTGTC AGC GCA CGT GCA CGT AGG TGC CGG G-3') (SEQ ID NO: 8) (the ClaI site is underlined) for PhaC2 to obtain 1680-bp and 1683-bp PCR products, respectively. The PCR products were digested with NheI and MfeI (PhaC1) and with NheI and ClaI (PhaC2), and cloned into pNEW-gfp digested with same restriction enzymes to generate pNEW-phaC1 and pNEW-phaC2, respectively. The 2,100 bp fragment carrying the lactase gene (bgl) from *Bifidobacterium infantis* was amplified from pEBIG4 (Hung et al. 2001) using primers BGL-F-Nhe (5'-CGCTAGCAT GGA ACA TAG AGC GTT CAA GTG G-3') (SEQ ID NO: 9) (the NheI site is underlined) and BGL-R-Sac (5'-CGAGCTCTT ACA GCT TGA CGA CGA GTA CGC CG-3') (SEQ ID NO: 10) (the SacI site is underlined). For the amplification of esterase gene (1,800 bp, estI) from *Lactobacillus casei*, pCESTa (Choi, et al. 2004) was used as a template with primers EST-F-Nhe (5'-CGCTAGCAT GGA TCA ATC TAA AAC AAA TCA AAA C-3') (SEQ ID NO: 11) (the NheI site is underlined) and EST-R-Sac (5'-CGAGCTCTT ATT TAT TTG TAA TAC CGT CTG C-3') (SEQ ID NO: 12) (the SacI site is underlined). These NheI-SacI fragments of bgl and est were then replaced with a gfp gene in the pNEW-gfp to form pNEW-bgl and pNEW-est, respectively. To amplify synthetic thrombin inhibitor peptide encoding gene with carrier protein (SFC120), pTSN-6A (Osborne et al., 2003) was used as a template with primers MFH-FNhe (5'-CGCTAGCAT GGC AAC TTC AAC TAA AAA ATT AC-3') (SEQ ID NO: 13) (the NheI site is underlined) and MFH-RMfe (5'-GCAATTGTT ATT GTA AAT ACT CTT CTG GAA TCG G-3') (SEQ ID NO: 14) (the MfeI site is underlined). The PCR product was digested with NheI and MfeI and the 456 bp fragment encoding carrier protein with synthetic thrombin inhibitor peptide was cloned into pNEW-gfp digested with same restriction enzymes to generate pNEW-mfh.

Host cell transformation and gene expression. pNEW vectors harbouring different genes of interest were transformed into various *E. coli* cells by chemical or electroporation methods (Sambrook and Russell, 2000). The transformed cells were grown at 37° C. in LB medium, and expression of genes under developed system was induced with 20 μg/ml cumate or as indicated.

Detection of gene expression. Detection of GFP was carried out by fluorescence microscopy, and quantified by using a SPECTRAFluor Plus (TECAN Austria Gmbh, Grodïg, Austria) under excitation and emission wavelengths of 485 and 508 nm, respectively. Concentration of GFP was calculated based on a linear relationship between concentration and fluorescence units determined using solutions of purified GFP (Qbiogene). The biomass (X) was determined by cell dry weight measurement of the samples (Moisture Analyzer MA 30, Sartorius).

Esterase activity was determined by a spectrophotometric method using paranitrophenyl caprylate (pNP-caprylate) as substrate. The rate of hydrolysis of pNP-caprylate at 37° C. was measured in 50 mM sodium phosphate buffer (pH 7.0) according to the method described previously (Kademi et al., 1999). One unit of activity was defined as the amount of enzyme that liberated 1 μmol of p-nitrophenol per min under the given assay conditions. The β-galactosidase activity was measured with o-nitrophenol-β-D-galactoside (ONPG) as a substrate and one unit of activity was defined as the amount of enzyme that liberated 1 μmol of o-nitrophenol per min (Sambrook and Russel, 2000). The protein concentration was estimated by the method of Bradford (Bradford, 1976) using the Bio-Rad protein assay kit with bovine serum albumin as a standard.

Western blotting. Integrative expression of repressor protein (cymR) was determined by western blotting using standard protocol. cymR was detected with rabbit anti-bCymR #422 antibody (0.1 g ml$^{-1}$) and a goat anti-rabbit IgG (H+L) HRP conjugate (0.1 μg ml$^{-1}$; Pierce cat #31460, West Grove, Pa.). Cells were lysed in SDS-PAGE sample buffer.

TABLE 1

Strains and Plasmids

| Strain or plasmid | Description | Reference or Source |
|---|---|---|
| *Pseudomonas* strains | | |
| fluorescens GK13 | Source of PhaC1 and C2 genes | Jaeger, et al., 1995 |
| putida F1 | Origin of cymR gene and operator sequence in the cmt operon, respectively. | Eaton, 1997 |
| *E. coli* strains | | |
| S-17Iλ pir | Tp$^r$ Sm$^r$, recA thi pro hsdR M$^+$ RP4: 2-Tc:Mu:Km Tn7 λpir | De Lorenzo et al., 1993 |
| Top10 | F– mcrA Δ(mrr-hsdRMS-mcrBC) φ80lacZΔM15 ΔlacX74 recA1 araD139 Δ(araleu) 7697 ga/U ga/K rpsL (StrR) endA1 nupG | Grant et al., 1990 |
| BL21(DE3)PLyS | F$^-$ ompT gal dcm lon hsdS$_B$(r$_B^-$ m$_B^-$) λ(DE3) pLysS(cm$^R$) | Novagen |
| DH5α | endA1 recA1 hsdR17(r$_K^-$ m$_K^+$) supE44 thi-1 gyrA96 φ80dlaCZΔM15 Δ(lacZYA-argF)U169 λ$^-$ | Hanahan, 1985 |
| K-12 | F$^-$ λ$^-$ rph-1 INV(rrnD, rrnE) | Jer sen, 1993 |

TABLE 1-continued

Strains and Plasmids

| Strain or plasmid | Description | Reference or Source |
|---|---|---|
| | Plasmids | |
| pBRI-cymR1 | pBRI80 plasmid containing one copy of cymR expression cassette | Choi, et al., 2006 |
| pNEW-pre | pET36 plasmid containing $P_{km}$-cymR expression cassettes, lack of T7 promoter and lac operator | This study |
| pCR2.1-TOPO | PCR cloning vector | Invitrogen Inc. |
| pCR-$P_{km}$-cymR | pCR2.1-TOPO plasmid containing $P_{km}$-cymR | This study |
| PCR-T5OP | pCR2.1-TOPO plasmid containing $P_{T5}$-operator | This study |
| pCR-bgl | pCR2.1-TOPO plasmid containing bgl | This study |
| pCR-est | pCR2.1-TOPO plasmid containing estl | This study |
| pCR-PhaC1 or C2 | pCR2.1-TOPO plasmid containing phaC1 or C2 | This study |
| pNEW | Newly constructed regulative expression vector | This study |
| pNEW-mfh | pNEW vector containing mfh fusion peptide expression cassette | This study |
| pNEW-phaC1 or 2 | pNEW vector containing PhaC1 or C2 expression cassette | This study |
| pNEW-bgl | pNEW vector containing lactase expression cassette | This study |
| pNEW-est | pNEW vector containing esterase expression cassette | This study |
| pNEW-gfp | pNEW vector containing gfp expression cassette | This study |
| pET36(b) | T7 based expression vector | Novagen |
| pCESTa | Esterase gene source | Choi et al., 2004 |
| pEBIG4 | Lactase gene source | Hung et al., 2001 |
| pTSN-6A | Source of fusion peptide mfh | Csborne et al., 2003 |

Results:

The basic mechanism of the cumate regulated gene expression in E. coli is depicted in FIG. 1. FIG. 1 shows a schematic diagram of the mechanism of action of the cumate-switchable expression system. (a) In the absence of a cumate, inducer, the repressor protein (cymR) is bound to the operator site upstream of the reporter gene or gene of interest, and block the transcription. (b) The presence of the cumate is necessary for transcription of gene of interest. The addition of cumate rapidly alters the inactive conformation (operator-cymR), facilitating the formation of the cymR-cumate complex and detached the cymR from the operator, and activating transcription of the downstream reporter gene. The cymR-cumate complex is unable to bind to operator site.

Figure 2:
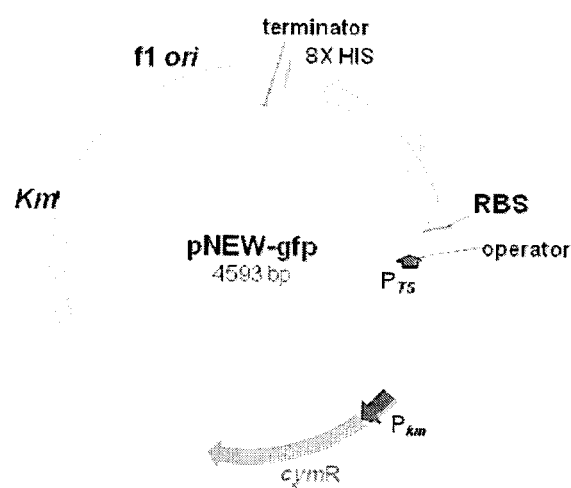
FIG. 2 is a physical map of plasmid pNEW-gfp designed for regulated expression of heterologous gene in *E. coli;*

Development of regulated expression vector pNEW-gfp. To develop a new generation of tightly regulated E. coli expression vectors, we applied T5 promoter-cumate operator carrying vector in cooperation with cymR repressor encoding gene in the same plasmid (FIG. 2).

Figure 3A:
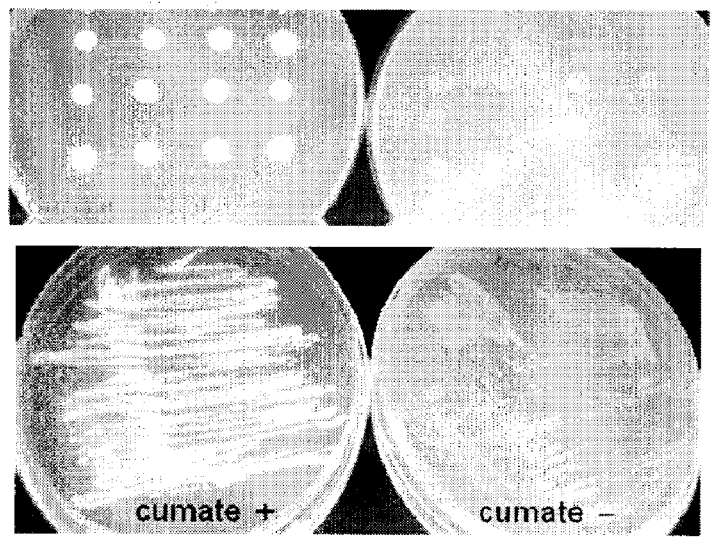
FIGS. 3A and 3B depict culture plate assays (A) and liquid culture assays (B) showing regulated expression of GFP in various *E. coli* strains as lost.
Figure 3B:
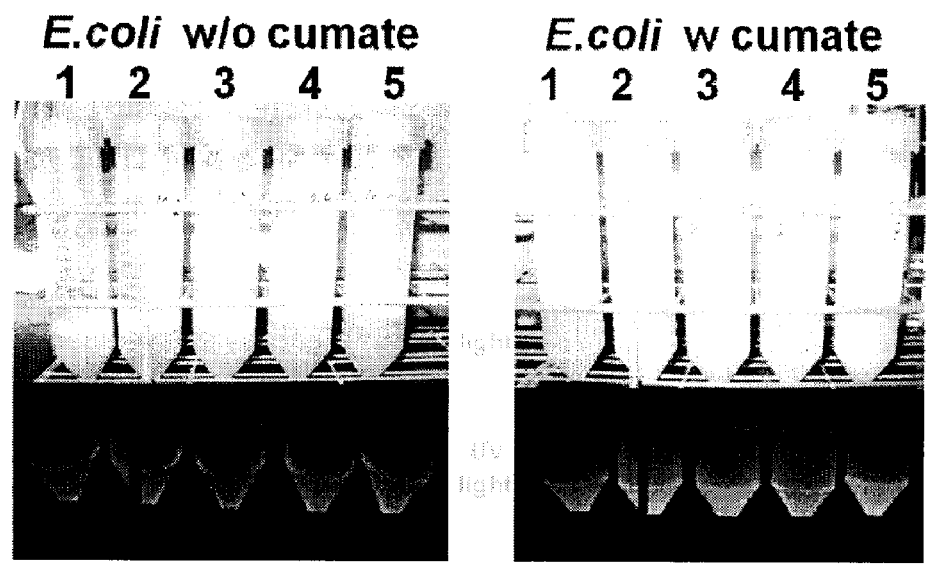

Validation of the developed expression system in E. coli hosts. Since T5 promoter is recognized by E. coli RNA polymerase, developed expression vectors can be applied to any type of E. coli strain, as shown in FIG. 3. FIG. 3A depicts plate assays, while FIG. 3B depicts liquid culture assays in culture tubes. In FIG. 3, the regulated expression of GFP (green fluorescent protein) in various E. coli strains as host is depicted. In FIG. 3B, tube #1 contains E. coli DH5α, tube #2 contains E. coli S17-1 λ/pir, tube #3 contains E. coli K12, tube #4 contains E. coli Top10, and tube #5 contains E. coli BL21 (DE3).

Heterologous gene expression. The performance or the cumate-regulated expression system was examined with various proteins as reporter.

Example 1

Green Fluorescent Protein (GFP) Expression

Figure 4:
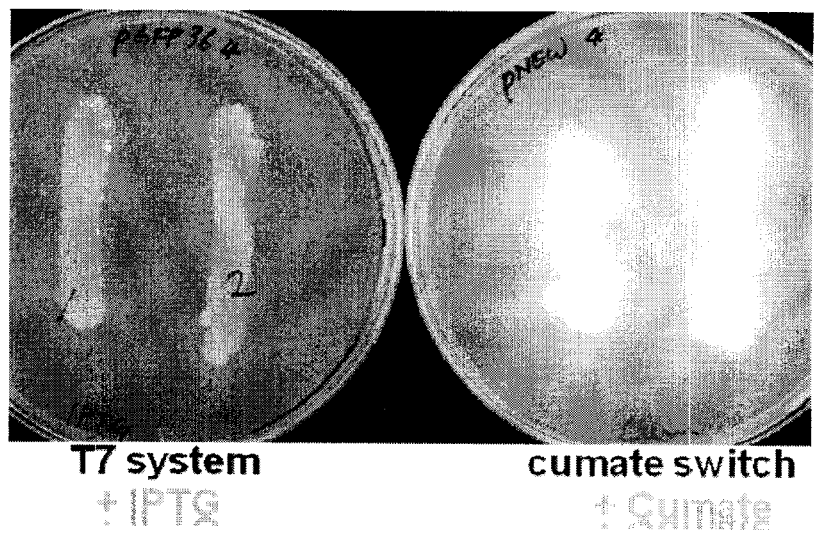
FIG. 4 depicts a comparison between T7 system and cumate system for green fluorescent protein (GFP) expression in plates containing IPTG (1 mM) and cumate (0.12 mM) as inducer, respectively.

FIG. 4 depicts a comparison between T7 system and cumate system for GFP expression in plates containing IPTG (1 mM) and cumate (0.12 mM) as inducer, respectively. It is evident from FIG. 4 that the cumate systems dramatically outperforms the IPTG system for expressing GFP in host cells.

Example 2

Expression of Polyhydroxyalkanoic Acids Synthetase (PhaC1 and PhaC2) Genes in E. coli Top10

Figure 5:
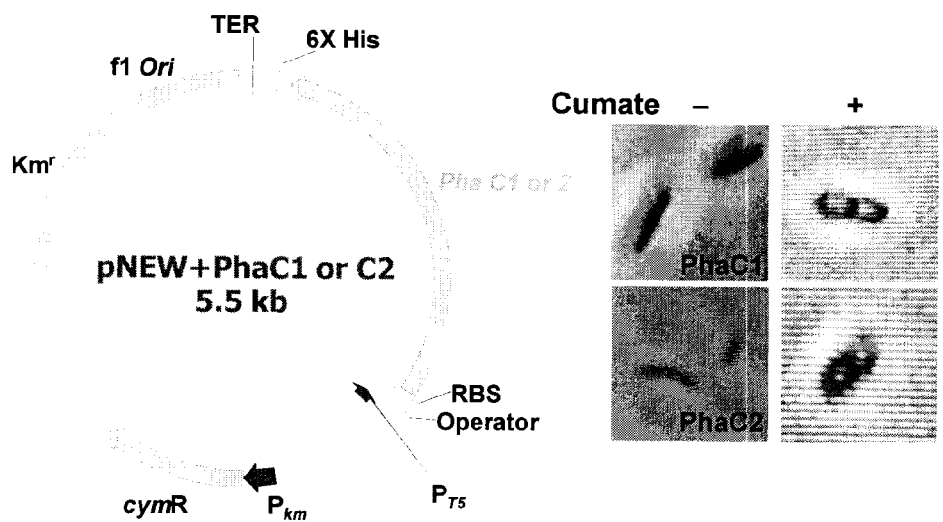
FIG. 5 is a physical map of pNEW-PhaC1, 2 and microscopic observation of the recombinant strains upon cumate induction (0.12 mM)

Genes encoding PhaC1 and C2 were amplified from Pseudomonas fluorescens GK13 and cloned into E. coli Top10 using cumate expression system. Amplified genes were successfully expressed in E. coli Top 10, and recombinant E. coli Top 10 produced PHB-like granules as shown in FIG. 5. FIG. 5 depicts a physical map of pNEW-PhaC1, 2 and microscopic observation of the recombinant strains upon cumate induction (0.12 mM).

Example 3

Production of Esterase Using Cumate Expression System in E. coli

Figure 6:
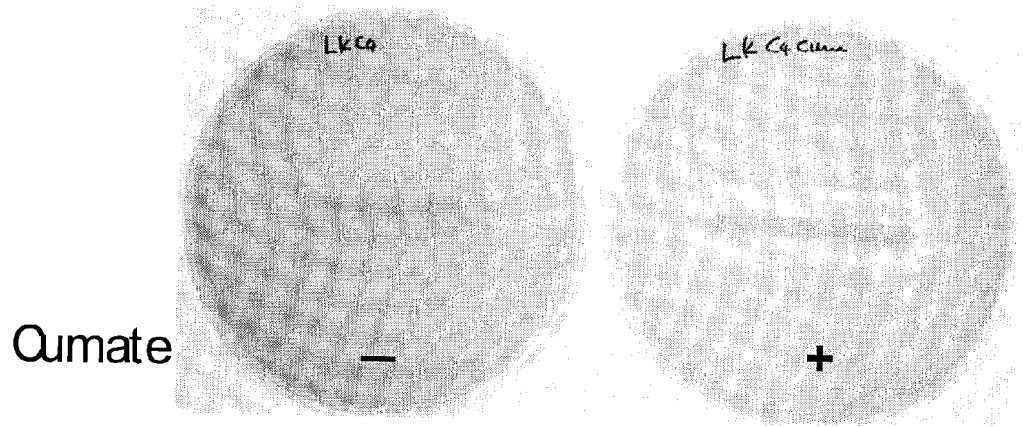
FIG. 6 depicts culture plates showing heterologous gene expression of esterase in *E. coli* Top10 using cumate expression system of the present invention without and with cumate as inducer.

FIG. 6 depicts heterologous gene expression of esterase in E. coli Top10 using the cumate expression system of the present invention. Recombinant strain was streaked on the plate containing 1% (v/v) tributyrin as a substrate of esterase without and with cumate (0.12 mM) as an inducer, respectively. It is evident from FIG. 6 that the cumate expression system was successful at heterologous gene expression of esterase.

Example 4

Production of Beta-Galactosidase Using Cumate Expression System in E. coli Top 10

Figure 7:
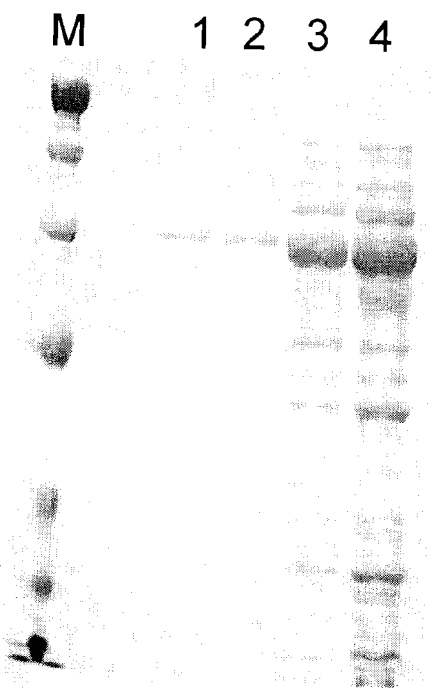
FIG. 7 depicts an expression profile of recombinant β-galactosidase on SDS-PAGE.

FIG. 7 depicts the expression profile of recombinant β-galactosidase on SDS-PAGE. Lane M is protein standard marker. Lane 1 is the first eluted sample as purified β-galactosidase using Ni-NTA mini affinity column. Lane 2 is the second eluted sample from the same column as Lane 1. Lanes 3 and 4 are crude protein samples 1 and 3 hr after induction, respectively. It is evident from FIG. 7 that β-galactosidase has been successfully expressed in E. coli Top 10 by the cumate expression system of the present invention.

Example 5

Figure 8:
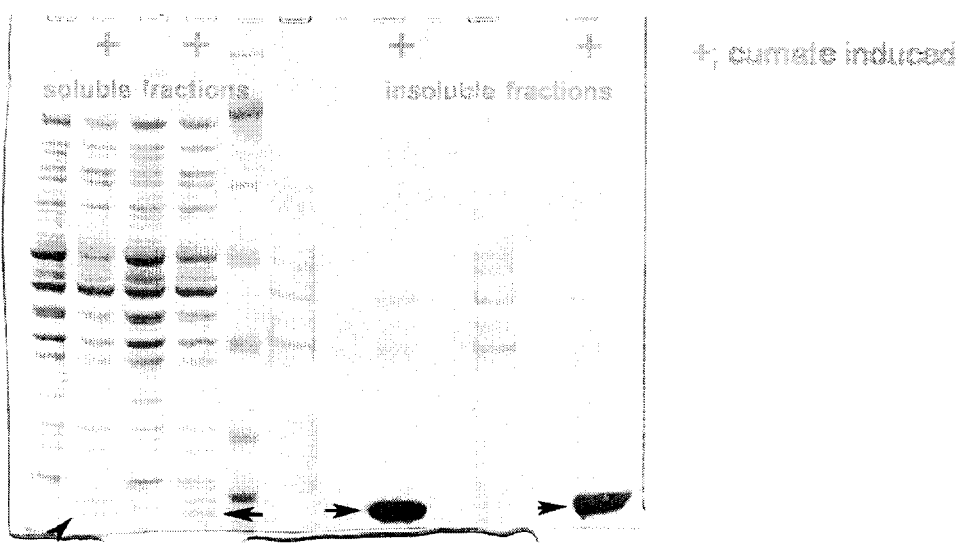
FIG. 8 depicts SDS-PAGE profile of soluble and insoluble fractions in the production of synthetic thrombin inhibitor peptide using carrier protein (SFC120) to form fusion peptide in *E. coli;*

Production of Synthetic Thrombin Inhibitor Peptide Using Carrier Protein (SFC120) to Form Fusion Peptide in E. coli FIG. 8 depicts the SDS-PAGE profile of soluble and insoluble fractions. Fusion peptide was produced in the form of inclusion body as expected, and the yield of fusion peptide reached about 85% of total cellular protein.

Example 6

Bench Top Fermentation

Figure 9A:
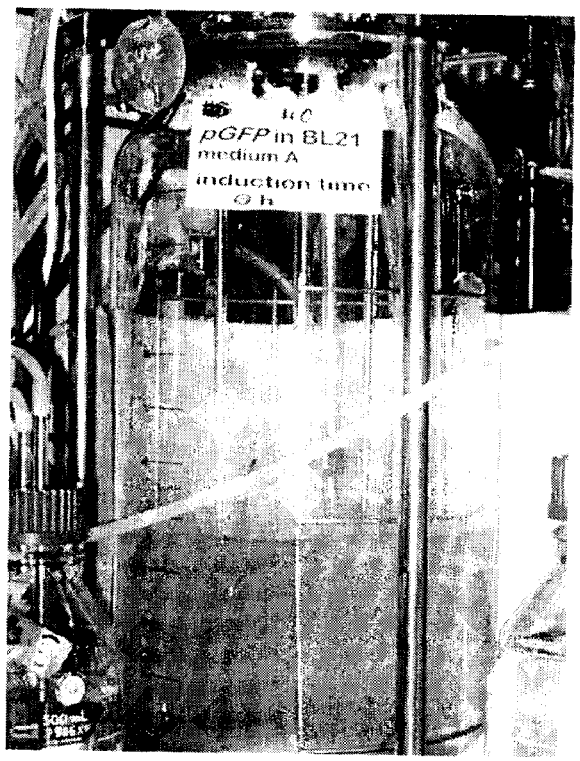
FIGS. 9A-9F depict fermenters at various stages of cell culture for recombinant *E. coli* cultures induced with IPTG or cumate; and, FIGS. 10A and 10B are graphs depicting time course green fluorescent protein (GFP) yield comparisons between T7 system and cumate system at concentrations of 100 μm inducer (A) and 1000 μm inducer (B).

FIG. 9A is a photograph of a fermenter with sterilized E. coli cultivation medium to show the original color of the cultivation medium. The original color is a gray/brown.

Figure 9B:
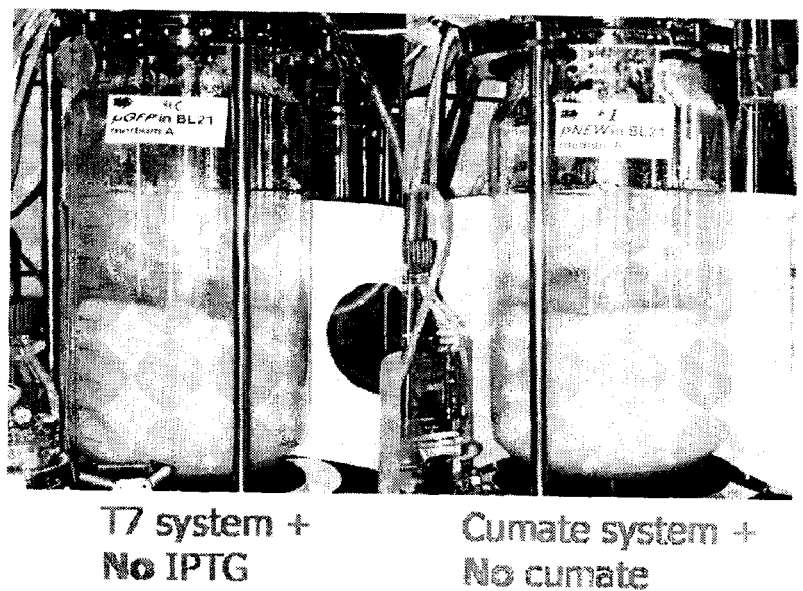

FIG. 9B is a photograph of two fermenters side-by-side, each fermenter containing cultivation medium and E. coli cells transformed with GFP. The fermenter on the left has the T7 expression system with no IPTG added yet. The fermenter in the right has the cumate expression system of the present invention with no cumate added yet. These photographs depict the cultures prior to induction by IPTG or cumate. The color of the cultures in each fermenter is the same, a light yellow/brown.

Figure 9C:
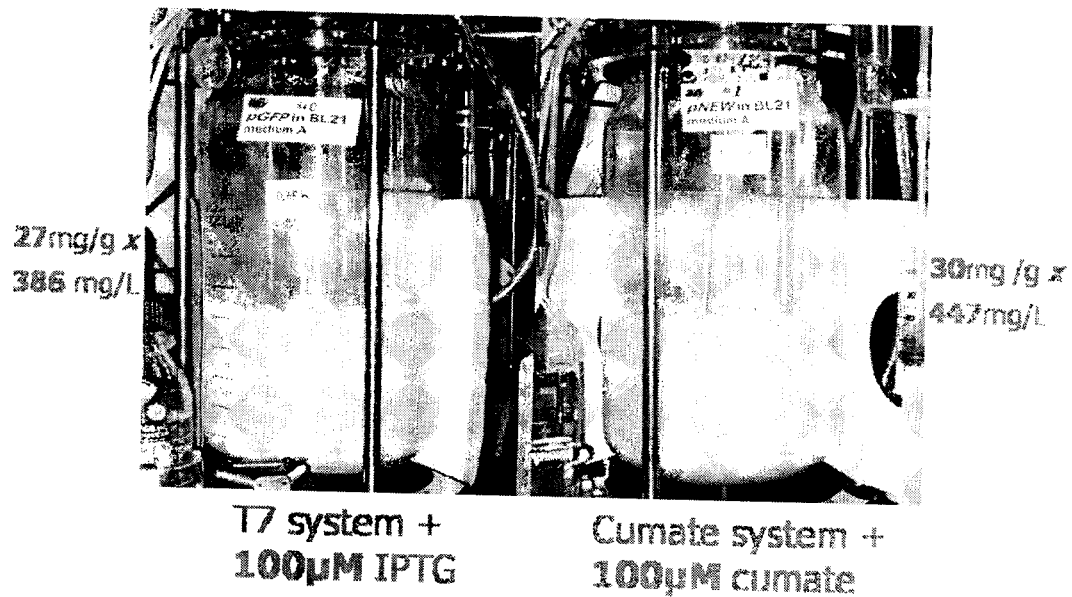

FIG. 9C is a photograph of the fermenters depicted in FIG. 9B at a time 45 minutes post induction with 100 μm IPTG (T7 system) and 100 μm cumate (cumate system). GFP yields are similar at this stage. The GFP yield for the IPTG induced system is 27 mg/g. The GFP yield for the cumate induced system is 30 mg/g. The color is a brighter yellow/green than in FIG. 9B.

Figure 9D:
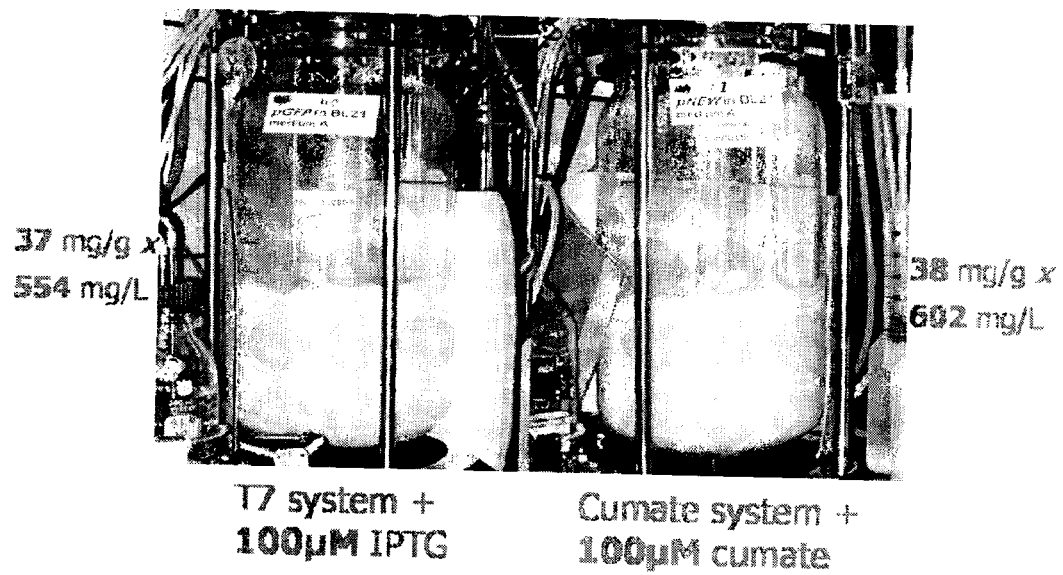

FIG. 9D is a photograph of the fermenters depicted in FIG. 9B at a time 1 hour post induction with 100 μm IPTG (T7 system) and 100 μm cumate (cumate system). GFP yields remain similar. The GFP yield for the IPTG induced system is 37 mg/g. The GFP yield for the cumate induced system is 38 mg/g. The color is a brighter yellow/green than in FIG. 9C.

Figure 9E:
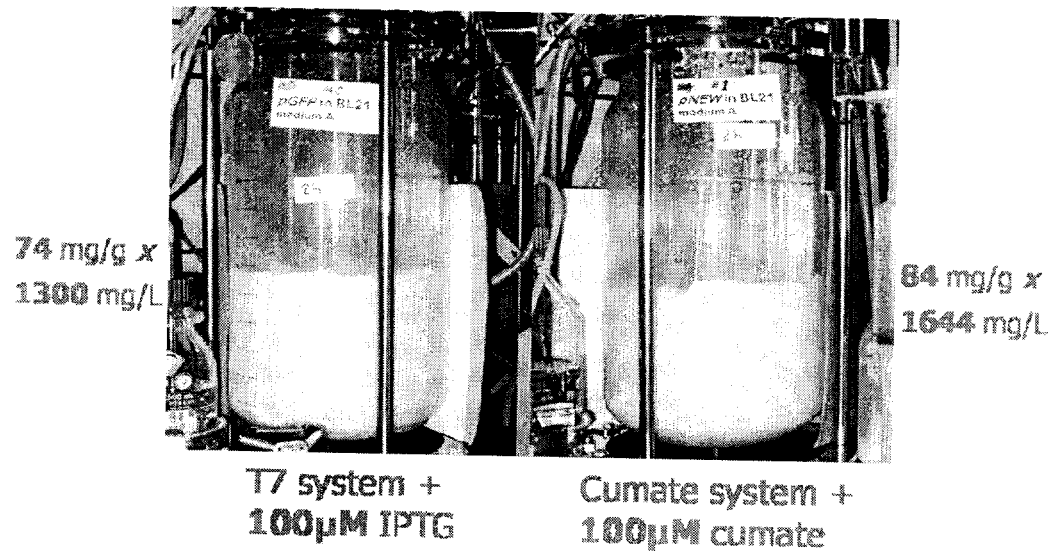

FIG. 9E is a photograph of the fermenters depicted in FIG. 9B at a time 2 hours post induction with 100 μm IPTG (T7 system) and 100 μm cumate (cumate system). At this point, GFP yields begin to differ that the cumate induced culture showing better yield. The GFP yield for the IPTG induced system is 74 mg/g. The GFP yield for the cumate induced system is 84 mg/g. The color is green and brighter than the colors in FIG. 9C. The medium in the fermenter with the cumate system is brighter green than the medium in the T7 system.

Figure 9F:
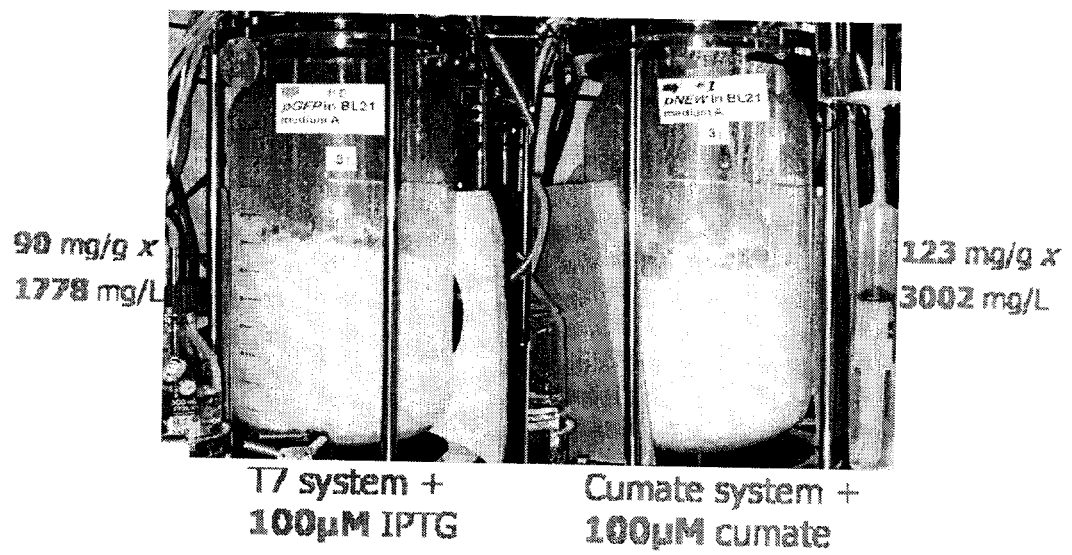

FIG. 9F is a photograph of the fermenters depicted in FIG. 9B at a time 3 hours post induction with 100 μm IPTG (T7 system) and 100 μm cumate (cumate system). GFP yield of the cumate induced culture is markedly greater than the IPTG induced culture. The GFP yield for the IPTG induced system is 90 mg/g. The GFP yield for the cumate induced system is 123 mg/g. The color is even brighter green than in FIG. 9E and the cumate induced system is brighter green than the IPTG induced system.

Figure 10A:
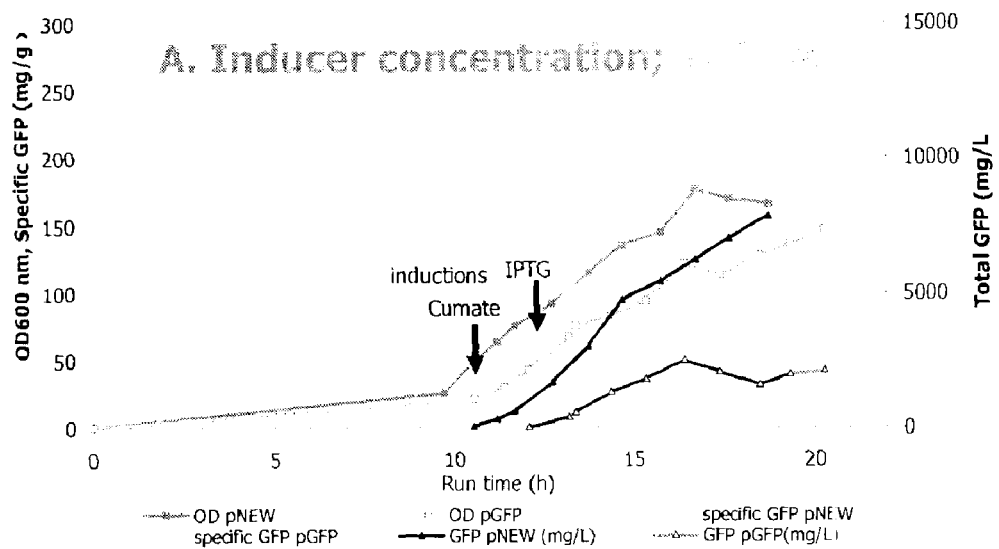
Figure 10B:
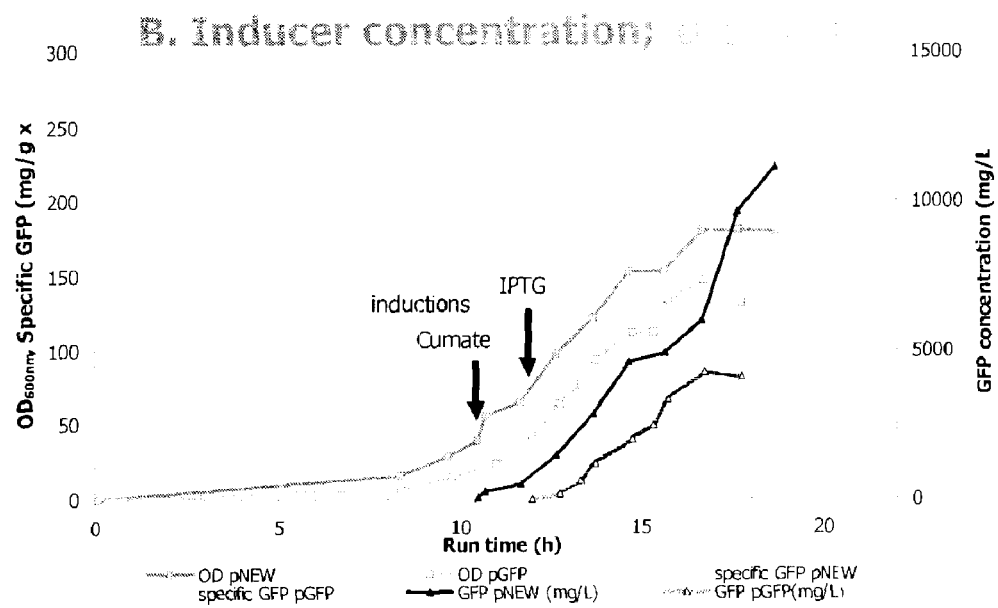

FIGS. 10A and 10B are graphs depicting the time course of GFP yield comparing the T7 system to the cumate system at different concentrations of inducers. For FIG. 10A, the concentration of inducer was 100 μm, while for FIG. 10B the concentration of inducer was 1000 μm. After 4 hours post induction, the IPTG induced GFP expression reached its maximum, whereas the cumate induced GFP expression continues even after 8 hours post induction (see also Tables 2 & 3). A similar phenomenon occurs when the cultures are induced with 1000 μM IPTG or cumate. The cumate induced GFP yield is more than double that of the IPTG induced culture. Furthermore, in cultures induced with 100 or 1000 μM cumate, expression of the GFP continues even though the culture has reached the stationary phase of growth. In other words, it is a form of resting cell GFP expression. The cumate induced culture remains healthy, no lysis occurred and no foaming was observed in contrast to the IPTG induced culture which after 8 hours post induction quickly began to lyse and GFP was released onto the culture medium.

TABLE 2

| Inducer conc. | | Induction Time (h) | | | | | | | |
|---|---|---|---|---|---|---|---|---|---|
| (μM) | Inducer | 1 | 2 | 4 | 5 | 6 | 7 | 8 | 9 |
| 100 | Cumate | 38 | 84 | 123 | 164 | 176 | 165 | 193 | 222 |
|  | IPTG | 37 | 74 | 90 | 96 | 85 | 58 | 68 | 67 |
| 1000 | Cumate | 36 | 71 | 110 | 141 | 149 | 155 | 249 | 289 |
|  | IPTG | 37 | 60 | 83 | 103 | 118 | 135 | 145 | — |

Table 2 shows results for the specific yield of GFP (mg/g x) up to 8 hours of induction for T7 and cumate expression systems in E. coli BL21(DE3)pLysS for two inducer concentrations. All results obtained were in defined medium A. The value 'x' is dry weight in g/L.

TABLE 3

| Inducer conc. | | Induction Time (h) | | | | | | | |
|---|---|---|---|---|---|---|---|---|---|
| (μM) | Inducer | 1 | 2 | 4 | 5 | 6 | 7 | 8 | 9 |
| 100 | Cumate | 602 | 644 | 3002 | 4719 | 5443 | 6194 | 6977 | 7838 |
|  | IPTG | 554 | 1300 | 1778 | 2486 | 2035 | 1567 | 1948 | 2090 |

TABLE 3-continued

| Inducer conc. | | Induction Time (h) | | | | | | | |
|---|---|---|---|---|---|---|---|---|---|
| (μM) | Inducer | 1 | 2 | 4 | 5 | 6 | 7 | 8 | 9 |
| 1000 | Cumate | 486 | 1459 | 2851 | 4593 | 4885 | 5989 | 9666 | 11150 |
| | IPTG | 606 | 1191 | 1966 | 2464 | 3340 | 4238 | 4079 | — |

Table 3 shows results for the total yield of GFP (mg/L) up to 8 hours of induction for T7 and cumate expression systems in E. coli BL21(DE3)pLysS for two inducer concentrations. All results obtained were in defined medium A.

REFERENCES

The contents of the entirety of each reference listed herein are incorporated by this reference.

Baneyx, F. 1999. Recombinant Protein Expression in *Escherichia coli*. *Curr. Opin. Biotechnol.* 10:411-421.

Bhandari, P. and J. Gowrishankar. 1997. An *Escherichia coli* host strain useful for efficient overproduction of cloned gene products with NaCl as the inducer. *J. Bacteriol.* 179: 4403-4406.

Bradford, M. M. 1976. A rapid and sensitive method for the quantitation of microgram quantities of protein utilizing the principle of protein-dye binding. *Anal. Biochem.* 72: 248-254.

Bujard, H., R. Gentz, M. Lanzer, D. Stüber, M. Müller, I. Ibrahimi, M. T. Häuptle, and B. Dobberstein. 1987. A T5 promoter-based transcription-translation system for the analysis of proteins in vitro and in vivo. *Methods Enzymol.* 155:416-433.

Choi, Y. J., C. B. Miguez, and B. H. Lee. 2004. Characterization and heterologous gene expression of a novel esterase from *Lactobacillus casei* CL96. *Appl. Environ. Microbiol.* 70: 3213-3221.

Choi, Y. J., L. Morel, D. Bourque, A. Mullick, B. Massie, C. B. Miguez. 2006. Bestowing inducibility on the cloned methanol dehydrogenase promoter ($P_{mxaF}$) of *Methylobacterium extorquens* by applying regulatory elements of *Pseudomonas putida* F1 *Appl. Environ. Microbiol.* 72:7723-7729.

De Lorenzo, V., L. Eltis, B. Kessler, and K. N. Timmis. 1993. Analysis of *Pseudomonas* gene products using lacI$^q$/Ptrp-lac plasmids and transposons that confer conditional phenotypes. *Gene* 123:17-24.

Eaton, R. W. 1996. p-Cumate catabolic pathway in *Pseudomonas putida* F1: cloning and characterization of DNA carrying the cmt operon. *J. Bacteriol.* 178:1351-1362.

Eaton, R. W. 1997. p-Cymene catabolic pathway in *Pseudomonas putida* F1: cloning and characterization of DNA encoding conversion of p-cymene to p-cumate. *J. Bacteriol.* 179:3171-3180.

Figge, J., C. Wright, C. J. Collins, T. M. Roberts, and D. M. Livingston. 1988. Stringent regulation of stably integrated chloramphenicol acetyl transferase genes by E. coli lac repressor in monkey cells. *Cell* 52:713-722.

Grant, S. G. N., J. Jessee, F. R. Bloom, and D. Hanahan. 1990. Differential Plasmid Rescue From Transgenic Mouse DNAs Into *Escherichia coli* Methylation-Restriction Mutants. *Proc. Natl. Acad. Sci. USA* 87:4645-4649.

Gupta, J. C., M. Jaisani, G. Pandey, and K. J. Mukherjee. 1999. Enhancing recombinant protein yields in *Escherichia coli* using the T7 system under the control of heat inducible $\lambda P_L$ promoter. *J. Biotechnol.* 68:125-134.

Hanahan, D. 1985. in DNA Cloning: A Practical Approach (Glover, D. M., ed.), Vol. 1, p. 109, IRL Press, McLean, Va.

Hung, M. N., Z. Xia, N. T. Hu, and B. H. Lee. 2001. Molecular and biochemical analysis of two β-galactosidases from *Bifidobacterium infantis* HL96. *Appl. Environ. Microbiol.* 67: 4256-4263.

Jaeger, K. E., A. Steinbüchel, and D. Jendrossek. 1995. Substrate specificities of bacterial polyhydroxyalkanoate depolymerases and lipases: bacterial lipases hydrolyze poly(omega-hydroxyalkanoates). *Appl. Environ. Microbiol.* 61:3113-3118.

Jensen, K. F. 1993. The *Escherichia coli* K-12 "wild types" W3110 and MG1655 have an rph frameshift mutation that leads to pyrimidine starvation due to low pyrE expression levels. *J. Bacteriol.* 175:3401-3407.

Kademi A., Fakhreddine, L., Abdelkader, N. & Baratti, J. C. '999. Effect of culture condition on growth and esterase production by the moderate thermophile *Bacillus circulans* MAS2. *J. Ind. Microbiol. Biotech.* 23:188-193.

Keyes, W. and A. Mills. 2003. Inducible systems see the light. *Trends Biotechnol.* 21:53-55.

Kosinski, M. J., U. Rinas, and J. E. Bailey. 1992. Isopropyl-beta-D-thiogalactopyranoside influences the metabolism of *E. coli*. *Appl. Microbiol. Biotechnol.* 36:782-784.

Lee, S. Y. 1996. High cell-density culture of *Escherichia coli*. *Trends Biotechnol.* 14:98-105.

Leigh, A. K., E. O, Sekyere, T. S. Stewart, P. J. Schofield, and M. R. Edwards. 1998. Cloning and Expression of a Prokaryotic Enzyme, Arginine Deiminase, from a Primitive Eukaryote *Giardia intestinalis*. *J. Biol. Chem.* 273: 4470-4477.

Osborne, M. J., Z. Su, V. Sridaran, and F. Ni. 2003. Efficient expression of isotopically labeled peptides for high resolution NMR studies: Application to the Cdc42/Rac binding domains of virulent kinases in *Candida albicans*. *J. Biomol. NMR*. 26:317-326.

Remaut, E., P. Stanssens and W. Fiers. 1981. Plasmid vectors for high-efficiency expression controlled by the $P_L$ promoter of coliphage lambda. *Gene* 15:81-93.

Rossi, F. M. and H. M. Blau. 1998. Recent advances in inducible gene expression systems. *Curr. Opin. Biotechnol.* 9:451-456.

Sambrook, J. and D. W. Russel. 2000. Molecular Cloning. third ed. (Cold Spring Harbor Laboratory, Cold Spring Harbor, N.Y. 2000).

Schein, C. H. and M. H. M. Noteborn. 1988. Formation of soluble recombinant proteins in *E. coli* is favored by lower growth temperature, *Bio/Technology* 6:291-294.

Staub, J. M., B. Garcia, J. Graves, P. T. J. Hajdukiewicz, P. Hunter, N. Nehra, V. Paradkar, M. Schlittler, J. B. Carroll, I. Spatola, D. Ward, Y. E. Guangning, and D. A. Russell. 2000. High-yield production of a human therapeutic protein in tobacco chloroplasts. *Nat. Biotechnol.* 18:333-338.

Studier, F. W. and B. Moffatt. 1986. Use of bacteriophage T7 RNA polymerase to direct selective high-level expression of cloned genes. *J. Mol. Biol.* 189:113-130.

Thiry, M. and D. Cingolani. 2002. Optimizing scale-up fermentation processes. *Trends Biotechnol.* 20:103-105.

Wang, Z. W., W. S. Law, and Y. P Chao. 2004. Improvement of the thermoregulated T7 expression system by using the heat-sensitive lacI. *Biotechnol. Prog.* 20:1352-1358.

Yogender P., J. C. Gupta and K. J. Mukherjee. 2001. Optimizing recombinant protein expression in the T7 system under the. control of the proUp promoter. *Biotechnol. Lett.* 23:41-46.

Yoon, S. H., M. J. Han, S. Y. Lee, K. J. Jeong, and J. S. Yoo. 2003. Combined transcriptome and proteome analysis of *Escherichia coli* during high cell density culture. *Biotech. Bioeng.* 81:753-767.

Miguez, Carlos B., et al., International Patent Publication WO 2007/022623 published Mar. 1, 2007.

Yu, Yan, et al., International Patent Publication WO 2006/037215 published Apr. 13, 2006.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

---

The invention claimed is:

1. An inducible expression system for transforming *E. coli* with a nucleic acid molecule of interest, the inducible expression system comprising:
   (a) a vector containing (i) a synthetic operator sequence of the cmt operon from *Pseudomomonas putida* F1 operatively linked to and downstream of a promoter for the operator, and (ii) a repressor sequence from the cym operon from *Pseudomomonas putida* F1 operatively linked to a promoter for the repressor; and,
   (b) an inducer for activating expression of the nucleic acid molecule of interest.

2. The expression system of claim 1, wherein the promoter for the operator comprises a partial T5 phage promoter.

3. The expression system of claim 1, wherein the promoter for the repressor comprises $P_{km}$, weak promoter.

4. The expression system of claim 1, further comprising a nucleic acid molecule of interest operatively linked to the operator.

5. The expression system of claim 4, wherein the nucleic acid molecule codes for a protein.

6. An *E. coli* host cell transformed with the expression system of claim 4.

7. A method of producing a protein comprising transforming an *E. coli* host cell with an expression system of claim 5; and, culturing the host cell in a culture medium under conditions in which the nucleic acid molecule will express the protein.

8. The method of claim 7 conducted in a fermenter.

9. The expression system of claim 5, wherein the nucleic acid molecule is heterologous to *E. coli*.

10. The *E. coli* host cell of claim 6, wherein the nucleic acid molecule codes for a protein.

11. The *E. coli* host cell of claim 10, wherein the inducer is p-cumate.

12. The expression system of claim 5, wherein the inducer is p-cumate.

* * * * *